United States Patent [19]
Ohkoshi

[11] Patent Number: 5,770,765
[45] Date of Patent: Jun. 23, 1998

[54] PROCESS FOR THE PRODUCTION OF HIGH-PURITY ISOPHTHALIC ACID

[75] Inventor: Fumio Ohkoshi, Kurashiki, Japan

[73] Assignee: Mitsubishi Gas Chemical Company, Inc., Tokyo, Japan

[21] Appl. No.: 890,006

[22] Filed: Jul. 8, 1997

[51] Int. Cl.$^6$ ................................................. C07C 51/16
[52] U.S. Cl. .............................................. 562/414
[58] Field of Search ................................ 562/414

[56] References Cited

U.S. PATENT DOCUMENTS

| | | |
|---|---|---|
| 4,933,492 | 6/1990 | Schroeder . |
| 5,189,209 | 2/1993 | Motoyama et al. . |
| 5,354,898 | 10/1994 | Schroeder . |
| 5,359,133 | 10/1994 | Goncharova . |
| 5,362,908 | 11/1994 | Schroeder . |

*Primary Examiner*—Samuel Barts
*Attorney, Agent, or Firm*—Wenderoth, Lind & Ponack

[57] ABSTRACT

A process for the production of high-purity isophthalic acid, which enables easy treatment of the PIA mother liquor, enables the recovery of the useful materials contained in the PIA mother liquor, decreases the discharge amount of water and enables the recycling of water to be used as a solvent, without additional investment and expenses, the process comprising the steps of a) separating a liquid-phase oxidation solution into an oxidation mother liquor and a crude isophthalic acid by crystallization and evaporating the oxidation mother liquor to form acetic acid vapor or a condensate thereof, b) dissolving the crude isophthalic acid in water, then catalytically hydrogenating, catalytically treating or oxidizing the resultant solution of isophthalic acid in water to form a purified solution, cooling the purified solution to crystallize isophthalic acid and separating the purified solution into a PIA mother liquor and a crystal of the isophthalic acid, and c) feeding the acetic acid vapor or condensate prepared by the evaporation of the oxidation mother liquor in step a) to a middle stage of a distillation column, feeding the mother liquor separated from the purified solution in the step b) to a top portion of the distillation column to carry out distillation, and discharging concentrated acetic acid containing aromatic carboxylic acids from a bottom portion of the distillation column.

6 Claims, No Drawings

PROCESS FOR THE PRODUCTION OF HIGH-PURITY ISOPHTHALIC ACID

FIELD OF THE INVENTION

The present invention relates to a process for the production of high-purity isophthalic acid which is a main raw material for a polyester resin used for industrial parts and components and general molding articles.

PRIOR ART

Isophthalic acid is generally produced by oxidizing a m-phenylene compound (mainly m-xylene) with molecular oxygen, mainly air, at a high temperature under a high pressure in acetic acid as a solvent in the presence of cobalt and manganese as a catalyst together with a bromine compound as a co-catalsyt or in the presence of cobalt as a catalyst together with a promoter such as acetaldehyde.

However, isophthalic acid obtained by the above liquid-phase oxidation generally has poor whiteness and contains a large amount of impurities such as 3-carboxybenzaldehyde (3CBA) and m-toluic acid, and the above isophthalic acid is therefore not suitable for use for producing a polyester by reacting it with glycol.

For producing a high-purity isophthalic acid by purifying the above crude isophthalic acid containing impurities such as 3CBA, there is known a purification method in which the isophthalic acid is oxidized or reduced or it is simply re-crystallized. Commercially, there is mainly carried out a method in which a crude isophthalic acid aqueous solution is catalytically hydrogenated at a high temperature and then the resultant solution is cooled and subjected to crystallization to obtain high-purity isophthalic acid.

In the above method, however, a mother liquor (to be referred to as "PIA mother liquor" hereinafter) which remains after the separation of the high-purity isophthalic acid contains aromatic carboxylic acids such as m-toluic acid and benzoic acid in addition to isophthalic acid in an amount equivalent to the solubility thereof. For disposing of the above PIA mother liquor, it is required to treat the aromatic carboxylic acids having high biochemical oxygen demand (BOD). Further, the disposal means a loss of valuable materials such as isophthalic acid and m-toluic acid which can be converted to isophthalic acid. Furthermore, the catalytic treatment step requires water in an amount greater than the amount of high-purity isophthalic acid to be produced.

The concentration of aromatic carboxylic acids in PIA mother liquor differs depending upon the quality of crude isophthalic acid, catalytic hydrogenation conditions, crystallization conditions or separation conditions. Generally, the PIA mother liquor contains approximately 500 to 700 ppm of isophthalic acid, approximately 100 to 1,000 ppm of m-toluic acid and approximately 10 to 500 ppm of benzoic acid. The PIA mother liquor is generally fed to a waste water treating apparatus, treated by an activated sludge process and discharged.

A commercially employed apparatus for producing isophthalic acid is a huge plant, and the amount of mother liquor to be treated for discharging is therefore large. For example, the amount of the mother liquor to be treated for discharging per apparatus is 5 to 100 m$^3$/h in a general commercial plant, and the investment of the apparatus for the discharged water treatment and the cost of the operation thereof are large.

Further, the above isophthalic acid and m-toluic acid being contained in the PIA mother liquor are useful materials for producing high-purity isophthalic acid, and the production cost of high-purity isophthalic acid increases due to the large expenses for the apparatus for the discharge treatment and the discharge of the useful materials.

SUMMARY OF THE INVENTION

It is an object of the present invention to provide a process for the production of high-purity isophthalic acid, which enables easy treatment of the PIA mother liquor.

It is another object of the present invention to provide a process for the production of high-purity isophthalic acid, which enables the recovery of the useful materials contained in the PIA mother liquor, decreases the discharge amount of water and enables the recycling of water to be used as a solvent, without additional investment and expenses.

According to the present invention, there is provided a process for the production of high-purity isophthalic acid by liquid-phase oxidizing a m-phenylene compound in an acetic acid solvent to form a crude isophthalic acid and purifying the crude isophthalic acid, which comprises the steps of a) separating the liquid-phase oxidation solution into an oxidation mother liquor and a crude isophthalic acid by crystallization and evaporating the oxidation mother liquor to form an acetic acid vapor or a condensate thereof, b) dissolving the crude isophthalic acid in water, then catalytically hydrogenating, catalytically treating or oxidizing the resultant solution of isophthalic acid in water to form a purified solution, cooling the purified solution to crystallize isophthalic acid and separating the purified solution into a mother liquor and a crystal of the isophthalic acid, and c) feeding the acetic acid vapor or condensate thereof prepared by the evaporation of the oxidation mother liquor in step a) to a middle stage of a distillation column, feeding the mother liquor separated from the purified solution in the step b) to a top portion of the distillation column to carry out distillation, and discharging concentrated acetic acid containing aromatic carboxylic acids from a bottom portion of the distillation column.

DETAILED DESCRIPTION OF THE INVENTION

The present inventor have made diligent studies on the process for the production of high-purity isophthalic acid which has the above problems, and have arrived at the present invention by finding the following. The PIA mother liquor which remains after the separation of high-purity isophthalic acid (crystal of isophthalic acid) in step 2) is recycled to a distillation step for removing reaction-formed water from hydrous acetic acid which is the oxidation mother liquor, and fed to the top portion of a distillation column as a reflux liquid, whereby useful components contained in the mother liquor can be recovered and the load of discharge can be decreased to a great extent.

The present invention will be explained in detail hereinafter.

In step a), a m-phenylene compound is oxidized in a liquid phase to produce a crude isophthalic acid. The m-phenylene compound refers to a compound having carboxyl groups on m-position or having, on m-positions, oxidizable substituents which can be converted to carboxyl groups by oxidation with air in a liquid phase. The substituents include methyl, ethyl, propyl, isopropyl, formyl and acetyl. The two substituents may be the same or different. As a m-phenylene compound, xylene is the most generally used.

As a solvent for the oxidation, hydrous acetic acid is used. The catalyst is selected from compounds of transition metals such as manganese, cobalt, iron, chromium and nickel. Further, a bromine compound is used as a co-catalyst in some cases. The catalyst is not specially limited so long as it can form manganese ion, cobalt ion, iron ion, chromium ion or nickel ion in an oxidation reactor. The co-catalyst is not specially limited so long as it can form bromide ion in an oxidation reactor.

When no bromide catalyst is used, acetaldehyde or methyl ethyl ketone may be used as a promoter in combination with a cobalt catalyst.

As an oxidizing agent, molecular oxygen is used, or generally, air is used. Air of which the oxygen concentration is increased by adding oxygen gas, or air of which the oxygen concentration is decreased by adding inert gas such as nitrogen gas, may be used.

The reaction temperature for the liquid-phase oxidation is generally in the range of from 160° C. to 220° C., and the pressure can be set in such a range that the hydrous acetic acid as a solvent can maintain a liquid phase. In an oxidation method using no bromine catalyst, a temperature of 160° C. or lower is employed in many cases.

The liquid-phase oxidation is generally carried out in one or more reactors. A reaction mixture obtained after the completion of the oxidation is fed to one reactor or a series of at least two reactors of which the pressures are consecutively decreased, to be cooled to temperature(s) corresponding to the pressures of the reactors by the flash cooling effect of the solvent. Most of a formed isophthalic acid is precipitated as a crystal to form a slurry.

The slurry is separated into a crude isophthalic acid cake and an oxidation mother liquor, for example, through a rotary vacuum filter or by a centrifugal separation method or some other proper method.

Part of the oxidation mother liquor is recycled as a solvent in step a) as it is or after it is oxidation-treated or reduction-treated. The remaining portion of the oxidation mother liquor is evaporated, generally, with an evaporation can or a thin film evaporator for removing water and other by-products formed in the oxidation, and separated mainly into acetic acid, vapor containing water and by-products having a low boiling point and an evaporation residue. The vapor is introduced to a distillation column in step c), and the evaporation residue is subjected to various steps to recover the catalyst, a useful component, and unuseful components are discharged.

The crude isophthalic acid cake is washed with acetic acid or water as required, and dried with a dryer to remove adhering solvent, to obtain a crude isophthalic acid.

Generally, the crude isophthalic acid obtained by liquid-phase oxidation contains a large amount of impurities including 3CBA, and the $OD_{340}$ value thereof as an index for a hue is below the level of a direct molding polymer material so that a purification step is generally required.

For the purification of the crude isophthalic acid to obtain a high-purity isophthalic acid, there are various methods such as catalytic hydrogenation, catalytic treatment, oxidation and crystallization. Any method can be used in the present invention, while the catalytic hydrogenation will be explained below since it is the most generally employed.

The catalytic hydrogenation is carried out in the presence of a metal selected from a Group VIII metal. The Group VIII metal includes palladium, platinum, ruthenium and rhodium, and palladium is particularly preferred. The above metal catalysts may be used in combination. The above catalyst is generally used in the form of a catalyst supported on a carrier. The carrier is generally selected from porous materials, while a carbon-based carrier is preferred in view of material qualities, and activated carbon, particulate coconut husk charcoal in particular, is preferred. The amount of the catalyst supported on the carrier is not specially limited, since the catalyst works effectively even if the amount is very small. For working the catalyst for a long period of time, however, the above amount is preferably 0.1 to 1% by weight.

The catalytic hydrogenation is carried out in an aqueous solution state at a high temperature under high pressure, and the temperature in the catalytic hydrogenation is at least 180° C. in the presence of hydrogen, preferably in the range of from 200° to 260° C.

The pressure in the catalytic hydrogenation can be set in any range so long as a liquid phase is maintained and so long as a hydrogen partial pressure suitable for the catalytic hydrogenation can be maintained, and generally, it is preferably in the range of from 10 to 60 atmospheric pressures.

Concerning the amount of hydrogen used for the catalytic hydrogenation, it is required to feed hydrogen in an amount of at least 2 mol per mole of 3CBA.

The time for the catalytic hydrogenation is not specially limited so long as the hydrogenation substantially proceeds. In the hydrogenation in a packed column, it is generally 1 to 60 minutes, preferably 2 to 20 minutes.

The catalytic hydrogenation is generally carried out by a continuous method.

For preventing an isophthalic acid product from containing a fine powder derived from the wearing of the catalyst carrier such as activated carbon, generally, the catalytically hydrogenated isophthalic acid aqueous solution is filtered, then, introduced to a 2- to 6-staged crystallizer connected in series or a batch-method crystallizer and consecutively pressure-decreased, whereby the aqueous solution is cooled by the evaporation of water and an isophthalic acid crystal is precipitated, to form a slurry.

The slurry is separated into an isophthalic acid cake and PIA mother liquor by a crystal separation method such as a rotary vacuum filter method or a centrifugal separation method.

Although not specially limited, the temperature for the separation of the slurry is generally approximately 70° to 160° C. When the separation is carried out at a high temperature, the obtained cake may be again converted to a slurry with water and the slurry is separated.

Step c) includes a distillation column in which the oxidation mother liquor is dehydrated for recycling an acetic acid solution. Vapor or condensate introduced from step a) contains water formed as a by-product by the oxidation in addition to acetic acid and by-products having low boiling points. The water is generally separated out of the system through the distillation column.

In step c), the vapor or condensate from an evaporation can or a thin-film evaporator is fed to a middle stage of the distillation column, and acetic acid which is dehydrated to such an extent that it can be recycled to the oxidation is obtained from the column bottom.

Generally, part of a distillate from the column top is discharged out of the system for attaining a determined separation efficiency, while the remaining portion is recycled to the column top.

In the above step, the reflux ratio [=amount of liquid to be recycled (m³/h)/amount of liquid to be discharged (m³/h)] is generally set at about 1/1 to about 10/1.

In the present invention, the PIA mother liquor from step b) is fed to the column top as a reflux liquid. The amount of the PIA mother liquor which can be treated in step c) is up to an amount equivalent to the reflux amount. When the reflux ratio is increased, naturally, the amount of the PIA mother liquor that can be treated increases. When the distillation column is operated at an unnecessarily large reflux ratio, however, a loss occurs, that is, the amount of required energy increases.

When the amount of the PIA mother liquor which is to be treated is smaller than the reflux liquid amount, a liquid to be discharged is recycled in an amount equivalent to a deficient amount. When the amount of the PIA mother liquor exceeds the reflux amount, the PIA mother liquor is concentrated. For the concentration, various heat sources recovered in a plant can be effectively used, while it is economical to use latent heat of steam distilled out from the top of the distillation column.

On the other hand, when the concentrated PIA mother liquor is fed, as a reflux liquid, to the top of the distillation column, a bubbling phenomenon takes place in a top portion of the distillation column, and when an extreme bubbling occurs, the distillation effect is sharply decreased, as will be shown in Referential Example to be described later.

The above bubbling phenomenon is caused when a crystal of isophthalic acid, etc., is present in the distillation column. The bubbling phenomenon is prevented by the following methods.

(1) A solid component (mainly composed of an isophthalic acid crystal) is separated and removed from the PIA mother liquor to be introduced, by a proper means such as filtering. This method is simple, while the unit operation required for the separation is additional, and the treatment of the separated isophthalic acid crystal is complicated.

(2) Metal ion is added to the PIA mother liquor to be fed to the column top. Cobalt or manganese is effective as a metal ion added to the PIA mother liquor. When it is added in an amount approximately equivalent to, or greater than, the molar amount of the isophthalic acid crystal present in the PIA mother liquor, the bubbling phenomenon can be completely prevented.

The above method (2) has been found by the present inventor for the first time. Cobalt and manganese are catalysts used in the oxidation step as is well known, and the presence thereof in acetic acid discharged from the bottom of the distillation column causes no problem on the oxidation.

Even when the PIA mother liquor is fed without concentrating it, the PIA mother liquor obtained in step c) may contain a small amount of an isophthalic acid crystal depending upon solid content separation means or under some other conditions. It is therefore preferred to provide a step of filtering the PIA mother liquor or add a metal ion in an amount which is sufficient for an estimated amount of an isophthalic acid crystal.

When the PIA mother liquor or its concentrated liquid is fed to the top of the distillation column, preferably, the PIA mother liquor is adjusted to a temperature approximately equivalent to the temperature of a distillate from the column top, specifically, to a temperature in the range of between the temperature of a distillate and a temperature lower than the temperature of the distillate by 50° C., so that a disorder of temperatures in the distillation column can be decreased.

According to the above process, the amount of aromatic carboxylic acids in water which is distilled out of the column top is small even when the PIA mother liquor fed to the column top contains aromatic carboxylic acids in an amount of several thousands ppm, and most part of valuable components in the PIA mother liquor can be recovered from the bottom of the distillation column in the form of an acetic acid aqueous solution, as will be shown in Examples to be described later.

When water distilled out of the column top is introduced into a waste water treating apparatus therefore, the load of waste water treatment is remarkably decreased as compared with a case where the PIA mother liquor is introduced without any treatment.

Further, the load of waste water treatment can be also decreased by a method in which water distilled out of the column top is recycled to step b) and used as a solvent for dissolving the crude isophthalic acid.

As shown in Examples, distillate water discharged from the column top contains only small amounts of aromatic carboxylic acids, by-products having low boiling points and acetic acid, and it can be therefore used as a solvent for the catalytic hydrogenation, while it is preferred to provide an adsorption step using activated carbon.

EXAMPLES

The present invention will be more specifically explained with reference to Examples hereinafter. PIA mother liquor used as a raw material in Examples was analyzed by high-performance liquid chromatography and gas chromatography to show the following contents, and it was slightly opaque at room temperature.

| | |
|---|---|
| Isophthalic acid | 2,130 ppm |
| m-Toluic acid | 198 ppm |
| Benzoic acid | 111 ppm |

For distillation, an sieve tray type fractionating column having an internal diameter of 32 mm and having 70 stages of porous plates was used, and hydrous acetic acid having a water content of 18% was continuously fed to a middle stage of the distillation column. Concentrated acetic acid was continuously withdrawn from the bottom.

Example 1

Hydrous acetic acid was charged to the bottom of the distillation column, and heated to stabilize the system in an entire reflux state. Then, hydrous acetic acid having a water content of 18% was fed to the middle stage of the distillation column, and concentrated acetic acid was withdrawn from the bottom. The reflux ratio was set at 6. The operation was continued for about 20 hours, and when it was found that the entire system was brought into a stationary state, the column top was switched to discharging of an entire water, and at the same time, PIA mother liquor was introduced through a reflux line in an amount equivalent to the amount of a liquid which was so far under reflux. Then, the operation was continued for about 12 hours, and at this point of time, the concentrations of aromatic carboxylic acids in distillate water discharged from the column top were as follows.

| | |
|---|---|
| Isophthalic acid | 187 ppm |
| m-Toluic acid | 49 ppm |
| Benzoic acid | 24 ppm |

The above analysis values are approximately one tenth of the concentrations of the aromatic carboxylic acids in the PIA mother liquor, and it is shown that a major part of the aromatic carboxylic acids were recovered from the column bottom in the form of an acetic acid solution.

Referential Example 1

PIA mother liquor to be fed was concentrated to an amount of ⅓ of the initial amount by heating in advance, and the experiment in Example 1 was repeated. The concentrated PIA mother liquor was opaque, in which a crystal of isophthalic acid was precipitated. The concentrated PIA mother liquor including the opaque portion was analyzed to show the following.

| | |
|---|---|
| Isophthalic acid | 5,260 ppm |
| m-Toluic acid | 498 ppm |
| Benzoic acid | 251 ppm |

After the initiation of the feeding, it took a while before a bubbling was visually observed in a tray in a top portion of the distillation column. At the same time, a solid substance on a tube wall were observed, and this phenomenon was brought into an intense state.

Example 2

The experiment in Referential Example 1 was repeated except that the concentrated PIA mother liquor was replaced with a filtrate prepared by filtering a concentrated PIA mother liquor through a 3G glass filter. The filtrate was analyzed to show the following.

| | |
|---|---|
| Isophthalic acid | 327 ppm |
| m-Toluic acid | 355 ppm |
| Benzoic acid | 224 ppm |

The operation was continued for about 12 hours, and at this point of time, the concentrations of aromatic carboxylic acids in distillate water discharged from the column top were as follows.

| | |
|---|---|
| Isophthalic acid | 28 ppm |
| m-Toluic acid | 97 ppm |
| Benzoic acid | 60 ppm |

The above analysis values are approximately one fifth of the concentrations of the aromatic carboxylic acids in the PIA mother liquor, and it is shown that a major part of the aromatic carboxylic acids were recovered from the column bottom in the form of an acetic acid solution. Further, it is seen that the bubbling phenomenon observed in the tray in a top portion of the distillation column in Referential Example 1 was caused by an isophthalic acid crystal.

Example 3

The experiment in Referential Example 1 was repeated except that manganese acetate in an amount of 1,740 ppm as a manganese atom was introduced into the fed liquid. The above amount was nearly equivalent to the molar amount of isophthalic acid in the fed liquid. The operation was continued for about 12 hours, and at this point of time, the concentrations of aromatic carboxylic acids in distillate water discharged from the column top were as follows.

| | |
|---|---|
| Isophthalic acid | 95 ppm |
| m-Toluic acid | 116 ppm |
| Benzoic acid | 43 ppm |

Referential Example 2

The experiment in Example 3 was repeated except that manganese acetate in an amount of 870 ppm as a manganese atom was introduced into the fed liquid. The above amount was nearly equivalent to ½ of the molar amount of isophthalic acid in the fed liquid. After the initiation of the feeding, it took a while before a bubbling was visually observed in a tray in a top portion of the distillation column, while the bubbling was far more moderate than that in Referential Example 1.

The results of Example 3 and Referential Example 2 show the following. An isophthalic acid crystal in the feed liquid is converted to a soluble compound with a manganese ion, so that the bubbling did not take place. When the amount of the manganese ion is equivalent to, or greater than, the molar amount of the isophthalic acid, the bubbling can be completely prevented.

Example 4

The experiment in Referential Example 1 was repeated except that cobalt acetate in an amount of 1,876 ppm as a cobalt atom was added to a fed liquid. The above amount was nearly equivalent to the molar amount of isophthalic acid in the fed liquid. The operation smoothly proceeded, and nothing appeared unusual in the distillation column. The operation was continued for about 12 hours, and at this point of time, the concentrations of aromatic carboxylic acids in distillate water from the column top were as follows.

| | |
|---|---|
| Isophthalic acid | 88 ppm |
| m-Toluic acid | 97 ppm |
| Benzoic acid | 54 ppm |

Referential Example 3

The experiment in Example 3 was repeated except that the amount of cobalt acetate was changed to 934 ppm as a cobalt atom. The above amount was nearly ½ of the molar amount of isophthalic acid in the fed liquid. After the initiation of the feeding, it took a while before a bubbling was visually observed in a tray in a top portion of the distillation column, while the bubbling was far more moderate than that in Referential Example 1.

The results of Example 4 and Referential Example 3 show the following. An isophthalic acid crystal in the feed liquid is converted to a soluble compound with a cobalt ion, so that the bubbling did not take place. When the amount of the cobalt ion is equivalent to, or greater than, the molar amount of the isophthalic acid, the bubbling can be completely prevented.

Example 5

The catalytic hydrogenation was carried out by using the distillate water obtained from the column top in Example 1 and crude isophthalic acid produced on a commercial scale as a raw material. Further, for comparison, an experiment was carried out using pure water.

The crude isophthalic acid used as a raw material was analyzed to show the following.

| | |
|---|---|
| OD$_{340}$ | 0.831 |
| 3CBA | 831 ppm |

A 2-liter pressure-resistant container made of stainless steel was charged with 300 g of the crude isophthalic acid and 900 g of water. The pressure-resistant container was equipped with a stirrer, a heater and a gas-introducing inlet, and further equipped with a catalyst cage which was movable electromagnetically upwardly and downwardly by external operation.

The catalyst cage was charged with 16 g, as a wet amount, of a palladium/carbon catalyst. The charged catalyst had been continuously used in a catalytic hydrogenation purification apparatus on a commercial scale for about 1 year, and it was cleaned of contaminating substances with a thin ammonia aqueous solution and then fully washed with water.

The catalyst cage was suspended in an upper portion of the pressure-resistant container made of stainless steel. Atmosphere in the container was fully purged several times by introducing a hydrogen gas through the gas-introducing tube, and the hydrogen gas was charged up to a pressure of 10 kg/cm$^2$ G. The liquid in the stainless steel container was heated with stirring, and when it was found that the temperature was stabilized at 235° C., the catalyst cage was moved downwardly until it was sunk in the liquid. After 20 minutes, the catalyst cage was moved up, and then the liquid was temperature-decreased. The liquid was cooled nearly to room temperature, and then a formed slurry was filtered through a G3 glass filter. The resultant cake was washed with pure water having a temperature of about 90° C. and dried at 110° C. to give high-purity isophthalic acid.

The high-purity isophthalic acid obtained by using pure water or the distillate water obtained in Example 1 was analyzed to show the following.

| (Water used) | (OD$_{340}$) | (3CBA) |
|---|---|---|
| Pure water | 0.188 | 8.9 ppm |
| Distillate water obtained in Example 1 | 0.196 | 7.2 ppm |

In these experiments, nothing unusual took place in the reaction, and differences in the evaluation results of the obtained isophthalic acids were within an allowable range of errors.

The experimental results of the above Examples and Referential Examples can be summarized as follows.

(1) When the PIA mother liquor is fed to the distillation column top as a reflux liquid and all of the distillate water from the column top is discharged, the concentrations of aromatic carboxylic acids in the distillate water were decreased to about 1/10 of those in the feed mother liquor.

(2) When the PIA mother liquor is fed to the distillation column top as a reflux liquid after it is concentrated, an isophthalic acid crystal which is precipitated in the PIA mother liquor forms a core to cause a bulling phenomenon in the upper portion of the distillation column.

(3) When the concentrated PIA mother liquor is fed to the distillation column top after an isophthalic acid crystal is removed by filtering, the bubbling phenomenon does not take place in the distillation column.

(4) When manganese ion or cobalt ion in an amount equivalent to isophthalic acid in the PIA mother liquor is added to the concentrated PIA mother liquor, the bubbling phenomenon does not take place in the distillation column.

(5) The distillate water from the column top can be used as a solvent for the catalytic hydrogenation of isophthalic acid.

When PIA mother liquor is fed for the reflux in an acetic acid dehydration column according to the process of the present invention, a major part of aromatic carboxylic acids in the PIA mother liquor can be recovered in the form of a solution thereof in acetic acid from the dehydration column bottom, and the acetic acid is recycled to the oxidation step. As a result, useful components such as isophthalic acid and m-toluic acid are effectively used, so that the yield of isophthalic acid increases and that the load of waste water treatment in the production of high-purity isophthalic acid can be remarkably reduced.

Further, the distillate water from the distillation column top is used as water in the purification step, and the amount of waste water is therefore decreased, so that the load on a waste water treating apparatus can be remarkably decreased.

The present invention enables the recovery of useful components in PIA mother liquor without any special investment or expenses, and the present invention therefore has a large industrial significance.

What is claimed is:

1. A process for the production of high-purity isophthalic acid by liquid-phase oxidizing a m-phenylene compound in an acetic acid solvent to form a crude isophthalic acid and purifying the crude isophthalic acid, which comprises the steps of a) separating the liquid-phase oxidation solution into an oxidation mother liquor and a crude isophthalic acid by crystallization and evaporating the oxidation mother liquor to form acetic acid vapor or a condensate thereof, b) dissolving the crude isophthalic acid in water, then catalytically hydrogenating, catalytically treating or oxidizing the resultant solution of isophthalic acid in water to form a purified solution, cooling the purified solution to crystallize isophthalic acid and separating the purified solution into a mother liquor and a crystal of the isophthalic acid, and c) feeding the acetic acid vapor or condensate prepared by the evaporation of the oxidation mother liquor in step a) to a middle stage of a distillation column, feeding the mother liquor separated from the purified solution in the step b) to a top portion of the distillation column to carry out distillation, and discharging concentrated acetic acid containing aromatic carboxylic acids from a bottom portion of the distillation column.

2. A process according to claim 1, wherein the purified solution is a solution obtained by the catalytic hydrogenation of the solution of the crude isophthalic acid in water.

3. A process according to claim 1, wherein the mother liquor from step b) is fed to the top portion of the distillation column after solid components are removed therefrom in advance.

4. A process according to claim 1, wherein the mother liquor from step b) is fed to the top portion of the distillation column after a manganese compound and/or a cobalt compound are/is added.

5. A process according to claim 1, wherein distillate water from the top portion of the distillation column is used as water for dissolving the crude isophthalic acid in step b).

6. A process according to claim 1, wherein part of the oxidation mother liquor is evaporated and fed to the middle stage of the distillation column and the rest thereof is used as a solvent for the liquid phase oxidation.

* * * * *